United States Patent [19]

Lustgarten et al.

[11] 4,412,015

[45] Oct. 25, 1983

[54] DENTAL FILLER MATERIAL CONTAINING ZEOLITE FOR DENTAL COMPOSITE AND METHOD OF MANUFACTURE

[76] Inventors: Stewart J. Lustgarten, 73 Dalton Rd., Holliston, Mass. 01746; Jürgen Engelbrecht, Kanalstrasse 37, Hamburg 76, Fed. Rep. of Germany

[21] Appl. No.: 260,394

[22] Filed: May 4, 1981

[30] Foreign Application Priority Data

Sep. 12, 1980 [DE] Fed. Rep. of Germany ....... 3034374

[51] Int. Cl.$^3$ .......................... C08K 9/04; A61K 6/02
[52] U.S. Cl. .................................... 523/116; 523/117; 523/203; 523/209; 523/212; 524/450; 428/405; 428/406; 428/407; 260/998.11
[58] Field of Search ............. 260/42.15, 42.52, 998.11; 428/405, 406, 407; 523/115, 116, 117; 524/444, 524/450

[56] References Cited

U.S. PATENT DOCUMENTS

| | | | |
|---|---|---|---|
| 3,066,112 | 11/1962 | Bowen | 260/42.15 |
| 3,519,593 | 7/1970 | Bolger | 524/461 |
| 3,625,916 | 12/1971 | Newman | 524/444 |
| 3,897,586 | 7/1975 | Coker | 428/407 |
| 3,914,341 | 10/1975 | Kliment et al. | 260/42.15 |
| 4,020,557 | 5/1977 | Rockett et al. | 260/42.15 |
| 4,028,325 | 6/1977 | King et al. | 200/42.15 |
| 4,029,632 | 6/1977 | Gross et al. | 260/998.11 |
| 4,150,012 | 4/1979 | Joos | 260/42.15 |
| 4,150,485 | 4/1979 | Lee et al. | 260/998.11 |
| 4,220,582 | 9/1980 | Orlowski et al. | 260/998.11 |
| 4,267,097 | 5/1981 | Michl et al. | 260/998.11 |
| 4,277,536 | 7/1981 | Podszun et al. | 428/402 |
| 4,281,991 | 8/1981 | Michl et al. | 260/42.15 |
| 4,297,266 | 10/1981 | Ibsen et al. | 260/42.15 |

FOREIGN PATENT DOCUMENTS 2086398 12/1982 United Kingdom .

OTHER PUBLICATIONS

Derwent Abst. 60883C/35 Dentsply 8-26-80 (Feb. 1, 1979 79US-008507), E. Pat.—14515.
Derwent Abst. 34955T/22 (SU-311638), "Dental Filling Material-with Zeolites to Improve Adhesion".
Derwent Abs. 41846C/24.
Derwent Abs. 41631C/24 Bayer DT2850917 (6-4-80).
Derwent Abst. 41632C/24 Bayer DT 2850918 (6-4-80).
Derwent Abst. 10155D/07 Mitsui Petro (2-4-81).
Derwent Abst. 27618D/16 Bayer (4-8-81) (EP-2-6-398).

Primary Examiner—Melvyn I. Marquis
Assistant Examiner—Herbert J. Lilling

[57] ABSTRACT

The dental filler material is formed from a selection of one or more finely divided inorganic particles of, barium containing glass or zeolite crystals with up to 100% of such particles having a coating thereon of a polymerized acrylate containing monomers or oligomers. The dental composite is formed using the dental filler material and a methacrylate based polymeric resin binder system.

11 Claims, No Drawings

DENTAL FILLER MATERIAL CONTAINING ZEOLITE FOR DENTAL COMPOSITE AND METHOD OF MANUFACTURE

This invention relates to a dental filler material and dental composite containing such filler material as well as to a method of manufacture of the filler material and the dental composite.

Filler materials commonly used in the preparation of restorative dental composites include particles of inorganic material such as silica, quartz and glass beads. Silicate or phosphate based minerals having either an amorphous or crystalline structure have also been used as dental reinforcing filler materials. These filler particles are added to a polymeric resin binder of any conventional composition which, in general, is acrylic based and which may be cold or heat cured or cured under ultraviolet or visible light radiation.

A direct filling material utilizing a finely divided filler and a resin binder has heretofore been described in U.S. Pat. No. 3,066,112 in which finely divided filler particles of fused silica is used to reinforce a methacrylate resin binder representing the reaction product of bisphenol A and glycidyl methacrylate. The silica is bonded to the resin by a silane keying agent. In U.S. Pat. No. 4,028,325 the filler material used is a composite of silica glass containing alkali and/or alkaline earth metal oxides. The addition of alkaline earth is suggested for increasing the workability of the dental composite. In U.S. Pat. No. 4,020,557 a ceramic reinforced polymer matrix composite is described as including a methacrylate based polymeric binder which is covalently bonded to a filler through a coupling silane keying agent. The filler material used is a calcium based silicate or phosphate base silicate mineral composition having a hardness of between 3 to 5 on the Moh's scale of hardness.

Ideally the inorganic reinforcing filler must contribute to the dental composite not only bulk and strength but should provide long term stability, abrasion resistance and hardness, inhibit polymerization shrinkage, provide a degree of x-ray opacity and have a relatively non sticky consistency before it is cured so as to permit the dental composite to be easily worked. The dental composite must also be polishable to a degree compatible with the lustre of natural teeth particularly for use in anterior restorations.

It is accordingly the principal object of the present invention to provide an inorganic filler material for use in dental restorative composites which will exhibit enhanced physical characteristics with increased dimensional stability and a high degree of polishability.

It has been discovered in accordance with the present invention that a dental composite material with particularly advantageous properties can be formed by employing an inorganic filler material comprising finely divided particles of silica or silicate glass, preferably barium containing glass and/or zeolite crystals of predetermined size with up to 100% of such particles provided with a coating of a polymerized acrylate containing monomers or oligomers.

The dental materials obtained by using the mineral inorganic filler particles formed in accordance with the present invention feature, in particular, the advantage that before hardening they have a non-sticky consistency and therefore can be easily formed. They furthermore are distinguished by an excellent polishing quality, increased abrasion resistance and hardness, a low thermal expansion coefficient and by low polymerization shrinkage. Moreover, the dental material formed in accordance with the present invention display good packing and tamping capability for use as a dental filler in the molar region. The enhanced properties of the dental material also lends itself for crown and bridge work as well as for the manufacture of artificial teeth.

The inorganic filler particles of the present invention may be selected of any conventional silica or silicate glass or mineral composition but is preferably a barium containing glass or a zeolite crystal or a combination thereof. The zeolite crystal is preferably an aluminosilicate with a stero lattice structure although any variety of zeolite containing aluminum and one of more other metallic elements particularly sodium, potassium or calcium may be used. The zeolite structure although preferably crystalline may also be amorphous. The barium containing glass can be prepared by melting together, at a minimum temperature (1100°-1300° C.) and for a minimum time (about 1 hour) necessary to obtain a homogeneous molten glass, the following glass making ingredients:

$SiO_2$—44 parts in mol percent
$BaF_2$—28 parts in mol percent
$Al_2O_3$—12 parts in mol percent
$B_2O_3$—16 parts in mol percent The glass can be melted, quenched and finely ground by means well known to the glass making art.

The inorganic filler particles should preferably have a Mohs hardness of no more than about 7 and preferably between 3 to 5 and should have a mean particle size of between about 0.01 to 20 microns and preferably between about 1–5 microns.

The selected inorganic filler particles should be enclosed within a synthetic covering preferably of a polymeric based acrylic resin which has been heat, cold or light polymerized. The synthetic material coating may possess, in accordance with the present invention, a mean thickness range from that of a thin film up to a thickness of 35 microns but is preferably between 1–3 microns in thickness. The thickness is advantageously selected in a manner such that the mean diameter of the coated particles lies between 0.1 and 50 microns although preferably between 1 to 10 microns.

The composition of the coating surrounding the filler particles may be selected without consideration of subsequent processing conditions. Thus, for instance, a material or hardening procedure may be selected to provide a particularly great strength and adhesion properties between the coating and the mineral filler particles or to achieve a particularly great hardness or other properties in the coating. By proper selection of coating hardness, a stepwise hardness transition from the mineral filler particles to the matrix may be obtained and thus particularly good properties for the composite may be realized.

Any hardenable synthetic material known to the art may be used to coat the filler particles. It is considered to be advantageous and preferred to use a synthetic material compatible with the resin binder in the dental composite. The resin binder may be any standard acrylic based polymeric binder used for preparing dental composites containing monomers or oligomers. A particularly preferred monomer or oligomer for use in formulating the resin binder matrix and as the synthetic coating is triethyleneglycol dimethacrylate.

It is also advantageous to use a silane keying agent such as methacryloxypropyltrimethoxysilane to promote adhesion between the binder and the filler material in a manner as fully disclosed in the prior art.

It should be understood that it is not essential to the present invention to use only inorganic filler particles coated with a hardenable monomer or oligomer. Rather the invention contemplates the use of a combination of conventional particles of inorganic filler mixed with polymerized coated particles of inorganic filler in mixing ratios of 1:10 to 10:1 by weight and in particular a ratio of 1:1.

The preparation of the mineral particles of the present invention may be carried out by treating the selected filler material after the material is properly sized with a solution containing the preferred monomer or oligomer in a suitable organic solvent. For example, the particles may be treated with a solution of triethyleneglycol dimethacrylate in methylene chloride $CH_2Cl_2$. The mixture is evaporated after treatment with the precipitated monomer heat polymerized. The resulting mixture may be milled and then sifted into an appropriate particle size range of preferably between 1 to 10 microns. In following this procedure agglomeration of the particles into a mass may be unavoidable requiring the added step, as above indicated, of milling the agglomerated mass of particles into the desired size range. This agglomeration may be avoided if the polymerization takes place in a liquid phase such as in the formation of pearl polymeride within the dispersion or when the polymerization occurs in a fluid bed, i.e., in a gaseous phase.

The coated filler particles in combination with, or exclusive of, uncoated filler particles may then be added in a conventional manner to form the major component, usually constituting at least 60 percent by weight, of a dental restorative composite. The uncoated particles are preferably treated with or a silane keying agent to promote adhesion and to render the particles hydrophobic. The dental resin composite may be packaged in a paste-paste or paste-liquid system suited for use by a dentist as is well known to the art. It should also be understood that the dental resin composite of the present invention may be packaged as a single paste system incorporating one or more conventional light initiators for effecting polymerization under eight ultraviolet or visible light. The advantages of the invention with reference to the consistency of the paste and the improved formability of the paste is a controlled variable depending upon the percentage of coated inorganic filler and particle size distribution.

The invention may be more fully understood by the following illustrative examples:

EXAMPLE 1

Preparation of polymerized urethane dimethacrylate coating on finely divided barium glass beads A total of 340 g of barium glass particles with a mean grain size of 5–10 microns is silanized in the conventional manner with methacryloxypropyltrimethoxysilane, and is mixed with 55 g of 7,7,9-trimethyl-4,13-dioxo-3,14-dioxa-5,12-diazahexadecane-1,16-diol dimethacrylate; 1,6 g of a free radical initiator such as lauroyl peroxide, as well as with 20 g of amorphous silicon dioxide and 200 ml of a solvent such as methylene chloride. After evaporation to a mash or slurrylike consistency the mixture is slowly stirred in water at 80° C. The precipating polymeride that contains the barium glass is filtered off and dried and then milled and fractionated to a desired grain size of between 1–10 microns.

EXAMPLE 2

Preparation of zeolite particles coated with polymerized triethyleneglycol dimethacrylate A total of 200 g sodium zeolite particles of a mean grain size between 1–4 microns is silanized in the conventional manner with methacryloxypropyltrimethoxysilane. Together with 50 g triethyleneglycol dimethacrylate, 8 g of azobisisobutyronitrile, and 200 ml methylene chloride, it is stirred until it is of loose consistency and is evaporated. Polymerization is carried out at 100° C. following the procedure of Example 1. The material so obtained is milled and fractionated into the desired grain-size range of between 1–10 microns.

EXAMPLE 3

Preparation of a dental material (a) Peroxide catalyst paste:
300 g of polymerized coated barium glass particles from Example 1 (grain-size 1–15 microns)
33 g amorphous silicon dioxide
43 g triethyleneglycol dimethacrylate
35 g 2,2-bis[4-3(3-methacryloxy-2-hydroxypropoxy)-phenyl]-propane
61 g 2-ethyl-2-hydroxymethyl-propanediol (1,3)-thrimethacrylate
3.6 g benzoyl peroxide The individual components are vigorously kneaded together and then subjected to vacuum.

(b) Amine accelerator paste:
The polymerized filler from Example 1 is used with all of the other components and all in the same amounts as used in the preparation of the Peroxide Paste (a) exclusive of the peroxide. In lieu of the peroxide, 3.6 g of NN-bis(2-hydroxypropyl)-3,5-dimethylaniline is used.

(c) Dental mass:
Equal parts of Paste A and Paste B are vigorously mixed for 30 seconds. The mixture obtained makes an excellent tooth-filling material. It hardens in a few minutes with very low polymerization shrinkage and can then be polished to a brilliant finish.

EXAMPLE 4

Preparation of a dental material

In accordance with the procedure followed in Example 3(a) and 3(b) a peroxide paste and an amine paste are produced from:
154 g polymerized particles from Example 2
200 g sodium zeolite (grain-size range 1–4 microns, silanized with methacryloxypropyltrimethoxysilane)
33 g amorphous silicon dioxide
43 g triethyleneglycol dimethacrylate
35 g 2,2-bis[4-(3-methacryloxy-2-hydroxypropoxy)-phenyl]-propane
61 g 2-ethyl-2-hydroxymethyl-propanediol(1,3)-trimethacrylate
3.6 g benzoyl peroxide or 3.0 g NN-bis-(2-hydroxyehyl)-p-toluidine.

Both pastes are mixed following Example 3(c). Again one obtains a mixture that is excellent as a tooth-filling material, particularly for the filling of molar cavities.

The dental materials prepared in accordance with the present invention distinguish themselves in that, with a high content of filler, they feature low polymerization contraction, low thermal expansion coefficients, good polishing capabilities, and high abrasion resistance.

What is claimed is:

1. A polishable dental material composite comprising: a binder resin of unreacted polymerizable acrylate containing monomors or oligomers; a free radical initiating agent for polymerizing said binder and finely divided particles of inorganic filler constituting at least 60% by weight of said composite with said inorganic filler composed primarily of zeolite crystals having a stereo lattice structure with a proportion of said inorganic filler having a coating thereon of a polymerized acrylate containing monomers or oligomers in a ratio of uncoated to coated filler particles between 1:10 and 10:1 by weight.

2. A dental material composite as defined in claim 1 wherein said coated particles of inorganic filler have a mean diameter within a size range of between 0.1 to 50 microns and with said polymerized coating having a mean thickness ranging between that of a thin film to 35 microns in thickness.

3. A dental material composite as defined in claim 2 wherein said polymerized coating has a mean thickness of between about 0.01 to 3 microns.

4. A dental material composite as defined in claims 2 or 3 wherein the coated particles of inorganic filler have a maximum Mohs hardness of 7.

5. A dental material composite as defined in claim 4 wherein said coating on said particles of inorganic filler comprises a dimethacrylate resin coupled to said particles by a silane keying agent.

6. A polishable dental filler material comprising finely divided inorganic particles having a mean particle size of between 0.1–50 microns and composed primarily of zeolite crystals containing aluminum and sodium, potassium or calcium with a proportion of said filler particles having a coating thereon of a polymerized acrylate containing monomers or oligomers in a ratio of uncoated to coated filler particles between 1:10 and 10:1 by weight.

7. A dental filler material as defined in claim 6 wherein said coating has a mean thickness of between about 0.01 to about 3 microns 8. A dental filler material as defined in claim 7 wherein said coated particles possess a maximum Mohs hardness of about 7.

9. A dental filler material as defined in claim 8 wherein said coating comprises a dimethacrylate resin coupled to said particles by a silane keying agent.

10. An inorganic filler material as defined in claim 9 wherein said coating is triethyleneglycol dimethacrylate.

11. A method for preparing a polishable dental composite material for use as a dental restorative comprising the steps of:

coating finely divided particles of zeolite crystals in a size range of from about 0.1 to 50 microns with an organosilane keying agent;

treating said silanized particles with a solution of an acrylate resin containing monomers or oligomers in a solvent;

polymerizing said acrylate resin to form an acrylate coating upon said finely divided particles;

fractionating said polymerized coated filler particles into a desired grain size range of between 1–10 microns;

combining said polymerized coated zeolite particles with uncoated inorganic filler particles in a ratio of between 1:10 to 10:1; and incorporating said combination of filler particles into a polymeric acrylic resin binder composition containing a free radical initiator in a first container and an aromatic amine accelerator in a second container.

* * * * *